(12) United States Patent
Bradshaw et al.

(10) Patent No.: US 7,998,747 B2
(45) Date of Patent: Aug. 16, 2011

(54) QUANTITATIVE DUAL-DYE PHOTOMETRIC METHOD FOR DETERMINING DILUTION IMPACT

(75) Inventors: John Thomas Bradshaw, Gorham, ME (US); Richard H. Curtis, Gorham, ME (US); Keith J. Albert, Auburn, ME (US); Tanya R. Knaide, South Portland, ME (US); Ceara McNally, Poland, ME (US); Alex L. Rogers, Gray, ME (US)

(73) Assignee: Artel, Inc., Westbrook, ME (US)

( * ) Notice: Subject to any disclaimer, the term of this patent is extended or adjusted under 35 U.S.C. 154(b) by 851 days.

(21) Appl. No.: 11/854,594

(22) Filed: Sep. 13, 2007

(65) Prior Publication Data

US 2008/0070317 A1    Mar. 20, 2008

Related U.S. Application Data

(60) Provisional application No. 60/825,744, filed on Sep. 15, 2006, provisional application No. 60/940,766, filed on May 30, 2007.

(51) Int. Cl.
*G01N 21/27* (2006.01)

(52) U.S. Cl. ........ 436/164; 436/179; 436/180; 422/919; 356/36; 356/246; 356/320; 356/432; 356/627

(58) Field of Classification Search ........................ None
See application file for complete search history.

(56) References Cited

U.S. PATENT DOCUMENTS

| | | | |
|---|---|---|---|
| 3,188,181 A * | 6/1965 | Peterson et al. | ............. 141/130 |
| 3,492,095 A | 1/1970 | Tillem | |
| 3,565,537 A | 2/1971 | Fielding | |
| 3,705,000 A | 12/1972 | Guerra | |
| 3,737,237 A | 6/1973 | Zurasky | |
| 3,869,211 A | 3/1975 | Watanabe et al. | |
| 3,920,580 A | 11/1975 | Mast | |
| 4,128,339 A | 12/1978 | Yamazaki et al. | |

(Continued)

FOREIGN PATENT DOCUMENTS

EP    0431578 B1    6/1991

(Continued)

OTHER PUBLICATIONS

Bradshaw, John Thomas et al. Multichannel verification system (MVS): A dual-dye ratiometric photometry system for performance verification of multichannel liquid delivery devices, 2005, JALA, vol. 10, p. 35-42.*

(Continued)

*Primary Examiner* — Arlen Soderquist
*Assistant Examiner* — Robert Xu
(74) *Attorney, Agent, or Firm* — Verrill Dana, LLP; Chris A. Caseiro

(57) ABSTRACT

The invention provides ways to determine the impact of diluting a solution wherein the diluting may be carried out for any of a variety of purposes. In one embodiment, the method enables accurate volume dispensation calculations independent of meniscus shape. In another embodiment, the method enables accurate determination of plate washing efficiency. In yet another embodiment, the method enables the accurate determination of dilution ratio over a plurality of dilution steps. The methods described may be carried out using one or more systems arranged to perform the steps. A kit of the invention includes instructions for carrying out the steps of the methods and, optionally, one or more solutions suitable for conducting photometric measurements.

5 Claims, 5 Drawing Sheets

Experimental demonstration of two stepwise dilution calculations for determining dilution accuracy.

| | Microtiter Plate | | |
|---|---|---|---|
| | 1 | 2 | 3 |
| Target Stepwise Dilution[a] | 1:20 | 1:2 | 1:2 |
| Target Total Dilution | 1:20 | 1:40 | 1:80 |
| Range Solution | C | C | C |
| Gravimetric Dilution | 19.89 | 39.67 | 79.14 |
| Photometric Dilution as Calculated using Equation (36), (n = 96) | NA[b] | 1.97 (± 0.22%) | 1.97 (± 0.24%) |
| % Inaccuracy | NA | -1.04 | -1.13 |
| Photometric Dilution as Calculated using Equation (41), (n = 96) | 19.54 (± 0.15%) | 1.97 (± 0.22%) | 1.97 (± 0.24%) |
| % Inaccuracy | -1.75 | -1.04 | -1.13 |

[a] All dilutions were made using a large volume gravimetric dilution procedure to minimize the error of multiple dilution steps. [b] This dilution step cannot be assessed with Equation (36) because the absorbance of the starting Range C cannot be measured.

U.S. PATENT DOCUMENTS

| | | | |
|---|---|---|---|
| 4,248,536 A | 2/1981 | Hijikata | |
| 4,305,659 A | 12/1981 | Bilstad et al. | |
| 4,354,376 A | 10/1982 | Greenfield et al. | |
| 4,357,105 A | 11/1982 | Loretz | |
| 4,405,235 A | 9/1983 | Rossiter | |
| 4,582,684 A | 4/1986 | Vogel et al. | |
| 4,595,561 A | 6/1986 | Thornton et al. | |
| 4,797,000 A | 1/1989 | Curtis | |
| 4,805,623 A | 2/1989 | Jobsis | |
| 5,064,282 A | 11/1991 | Curtis | |
| 5,092,677 A | 3/1992 | Curtis | |
| 5,125,747 A | 6/1992 | Sayegh et al. | |
| 5,244,813 A | 9/1993 | Walt et al. | |
| 5,247,345 A | 9/1993 | Curtis | |
| 5,258,308 A | 11/1993 | Freeman et al. | |
| 5,298,978 A | 3/1994 | Curtis et al. | |
| 5,492,673 A | 2/1996 | Curtis et al. | |
| 5,766,875 A | 6/1998 | Hafeman et al. | |
| 5,959,738 A | 9/1999 | Hafeman et al. | |
| 5,963,318 A | 10/1999 | Held | |
| 6,188,476 B1 | 2/2001 | Hafeman et al. | |
| 6,320,662 B1 | 11/2001 | Hafeman et al. | |
| 6,339,472 B1 | 1/2002 | Hafeman et al. | |
| 6,661,512 B2 | 12/2003 | Fernando et al. | |
| 6,741,365 B2 | 5/2004 | Curtis | |
| 7,061,608 B2 | 6/2006 | Curtis et al. | |
| 7,187,455 B2 | 3/2007 | Curtis | |
| 2002/0149772 A1 | 10/2002 | Halg | |
| 2003/0107738 A1 | 6/2003 | Curtis | |
| 2004/0246501 A1 | 12/2004 | Curtis | |
| 2005/0168737 A1 | 8/2005 | Bradshaw et al. | |
| 2007/0141709 A1 | 6/2007 | Albert et al. | |
| 2007/0161114 A1 | 7/2007 | Curtis et al. | |

FOREIGN PATENT DOCUMENTS

| | | | |
|---|---|---|---|
| JP | 07-167756 | * | 7/1995 |

OTHER PUBLICATIONS

Dong, Huijin et al. The Use of a Dual Dye Photometric Calibration Method to Identify Possible Sample Dilution from an Automated Multichannel Liquid-handling System, 2006, JALA, vol. 11, pp. 60-64.*

International Search Report and Written Opinion for corresponding PCT application No. PCT/US2007/020036, Mar. 27, 2008, 10 pp.

Taylor et al., "A Standard Operating Procedure for Assessing Liquid Handler Performance in High-Throughput Screening", Journal of Biomolecular Screening 7:554-569 (2002).

Cohn et al., "Precision Techniques for Measuring Liquid Quantity," Control Engineering, vol. 15, Jan. 1968, U.S., pp. 51-55 (5 pages).

Waring et al., "The Chemistry and Application of Dyes," 1990, Plenum Press, New York, U.S., p. 282 (2 pages).

Lubs, "The Chemistry of Synthetic Dyes and Pigments," Amer. Chem. Soc., Color and Chemical Constitution of Dyes, 1970, Hafner Publishing, Darien, CT, US, pp. 675-676 (3 pgs).

International Standard, ISO 8655-7, "Piston-operated volumetric apparatus—Part 7: Non-gravimetric methods for the assessment of equipment performance," Sep. 1, 2005, (27 pgs).

* cited by examiner

Figure 1. The approximate dilution range measurable by each MVS Sample Solution.

| Sample Solution | Red dye absorbance per pathlength (cm$^{-1}$) $(a_r = \varepsilon_{520} \cdot C)$ | Dilution Range |
|---|---|---|
| Range A | 3.75 | 1 – 1:4 |
| Range B | 15 | 1:4 – 1:20 |
| Range C | 75 | 1:20 – 1:100 |
| Range D | 185 | 1:100 – 1:400 |
| Range E | 740 | 1:400 – 1:2000 |

Figure 2. Experimental design defining the solution volumes added to each column in a microtiter plate.

| | 1 | 2 | 3 | 4 | 5 | 6 | 7 | 8 - 12 |
|---|---|---|---|---|---|---|---|---|
| A | 200 µL neat MVS Sample Solution | 100 µL from column 1 | 67 µL from column 2 | 50 µL from column 3 | 40 µL from column 4 | 33 µL from column 5 | 50 µL from column 6 | Empty |
| B | | + | + | + | + | + | + | |
| C | | 100 µL MVS Diluent | 133 µL MVS Diluent | 150 µL MVS Diluent | 160 µL MVS Diluent | 167 µL MVS Diluent | 150 µL MVS Diluent | |
| D | | | | | | | | |
| E | | | | | | | | |
| F | Remove 100 µL to column 2 | Remove 67 µL to column 3 | Remove 50 µL to column 4 | Remove 40 µL to column 5 | Remove 33 µL to column 6 | Remove 50 µL to column 7 | Remove 100 µL to waste | |
| G | | | | | | | | |
| H | | | | | | | | |

Figure 3. Experimental demonstration of a dual-dye absorbance method for determining dilution accuracy.

| | Microtiter Plate Column | | | | | | |
|---|---|---|---|---|---|---|---|
| | 1 | 2 | 3 | 4 | 5 | 6 | 7 |
| Target Stepwise Dilution[a] | 1 | 1:2 | 1:3 | 1:4 | 1:5 | 1:6 | 1:4 |
| Target Total Dilution[b] | 0 | 1:2 | 1:6 | 1:24 | 1:120 | 1:720 | 1:2880 |
| Range Solution | A | A | B | B/C | D | E | E |
| Volume Transferred (μL) | NA | 100 | 67 | 50 | 40 | 33 | 50 |
| Volume Remaining (μL) | 100 | 100 | 133 | 150 | 160 | 167 | 150 |
| % Inaccuracy of Stepwise Dilution[c] (n = 8) | NA[d] | −1.13% (± 0.32%)[e] | −2.47% (± 0.46%) | −3.40% (± 0.47%) | 2.53% (± 1.13%) | −2.06% (± 0.60%) | −3.89% (± 0.83%) |
| % Inaccuracy of Total Dilution[f] (n = 8) | 0.43% (± 0.25%) | −0.47% (± 0.11%) | −1.15% (± 0.37%) | −0.97% (± 0.68%) | 5.52% (± 2.21%) | 2.85% (± 1.66%) | −1.15% (± 1.94%) |

[a] Sample dilution from one plate column to the next. [b] Sample dilution for one plate column as compared to column 1. [c] Inaccuracy of the dilution ratio calculated using the dilution from Equation (36) as compared to the target stepwise dilution. [d] Column 1 was filled with neat solution, so no stepwise dilution occurred. [e] Coefficient of variation (%CV). [f] Inaccuracy of the dilution ratio calculated using the dilution from Equation (40) as compared to the target total dilution.

Figure 4 – Results from a multi-step 1:2 serial dilution method carried out in a 96-well microtiter plate.

| Dilution Type | 1 | 1:2 | 1:2 | 1:2 | 1:2 | 1:2 | 1:2 | 1:2 | 1:2 | 1:2 | 1:2 | 1:2 |
|---|---|---|---|---|---|---|---|---|---|---|---|---|
| Total Dilution | 0 | 1:2 | 1:4 | 1:8 | 1:16 | 1:32 | 1:64 | 1:28 | 1:256 | 1:512 | 1:1024 | 1:2048 |
| Range Solution | Range A | Range A | Range A | Range B | Range B | Range C | Range C | Range D | Range D | Range E | Range E | Range E |
| Column | 1 | 2 | 3 | 4 | 5 | 6 | 7 | 8 | 9 | 10 | 11 | 12 |
| Volume Transferred | 200 | 100 | 100 | 100 | 100 | 100 | 100 | 100 | 100 | 100 | 100 | 100 |
| Volume Remaining | 100 | 100 | 100 | 100 | 100 | 100 | 100 | 100 | 100 | 100 | 100 | 100 |
| % Inacc from initial | 0.78% | -1.07% | -1.07% | -2.38% | -2.01% | -3.33% | -2.51% | -2.55% | -0.08% | -0.16% | -1.23% | -0.91% |
| % Inacc of transfer | | -1.83% | -0.95% | -1.45% | -1.61% | -1.35% | 0.50% | -0.04% | -1.28% | -0.24% | -1.07% | 0.32% |
| %CV tip-to-tip | 0.39% | 0.54% | 0.16% | 0.30% | 0.37% | 0.35% | 0.23% | 0.38% | 0.43% | 0.41% | 0.37% | 1.10% |

Figure 5. Experimental demonstration of two stepwise dilution calculations for determining dilution accuracy.

| | Microtiter Plate | | |
|---|---|---|---|
| | 1 | 2 | 3 |
| Target Stepwise Dilution[a] | 1:20 | 1:2 | 1:2 |
| Target Total Dilution | 1:20 | 1:40 | 1:80 |
| Range Solution | C | C | C |
| Gravimetric Dilution | 19.89 | 39.67 | 79.14 |
| Photometric Dilution as Calculated using Equation (36), (n = 96) | NA[b] | 1.97 (± 0.22%) | 1.97 (± 0.24%) |
| % Inaccuracy | NA | -1.04 | -1.13 |
| Photometric Dilution as Calculated using Equation (41), (n = 96) | 19.54 (± 0.15%) | 1.97 (± 0.22%) | 1.97 (± 0.24%) |
| % Inaccuracy | -1.75 | -1.04 | -1.13 |

[a] All dilutions were made using a large volume gravimetric dilution procedure to minimize the error of multiple dilution steps. [b] This dilution step cannot be assessed with Equation (36) because the absorbance of the starting Range C cannot be measured.

QUANTITATIVE DUAL-DYE PHOTOMETRIC METHOD FOR DETERMINING DILUTION IMPACT

CROSS REFERENCE TO RELATED APPLICATIONS

The present application claims the priority benefit of U.S. provisional patent application Ser. No. 60/825,744, filed Sep. 15, 2006, entitled "QUANTITATIVE DUAL-DYE PHOTOMETRIC METHODS FOR DETERMINING VOLUME DISPENSE ACCURACY AND/OR THE CORRESPONDING DILUTION RATIO FOR VARIED LIQUIDS" of the present assignee. The present application also claims the priority benefit of U.S. provisional patent application Ser. No. 60/940,766, filed May 30, 2007, entitled "QUANTITATIVE DUAL-DYE PHOTOMETRIC METHODS FOR DETERMINING VOLUME DISPENSE ACCURACY AND/OR THE CORRESPONDING DILUTION RATIO FOR VARIED LIQUIDS" of the present assignee. The entire contents of those prior applications are incorporated herein by reference.

BACKGROUND OF THE INVENTION

1. Field of the Invention

The present invention relates to methods for determining the impact of diluting a solution. In particular, the present invention relates to a method for determining a volume of a solution mixed with a diluent. The present invention also relates to a method for determining the efficiency of removing one or more reagents from a vessel using a wash solution. The present invention further relates to a method for determining the dilution ratio for a solution under dilution.

2. Description of the Prior Art

Existing versions of the Multichannel Verification System ("MVS®"), which are commercially available from Artel, Inc. ("Artel") of Westbrook, Me. and are the subject of U.S. Pat. No. 6,741,365 and U.S. Pat. No. 7,187,455, include the use of equipment and aqueous sample solutions to determine the accuracy of dispensing devices over specified volume ranges. Additionally, an existing method which may be used to measure the volume of a non-aqueous sample solution created from an aqueous precursor is the subject of US Patent Application Publication No. 2007/0141709. The entire contents of U.S. Pat. No. 6,741,365, U.S. Pat. No. 7,187,455 and US Patent Application Publication No. 2007/0141709 are incorporated herein by reference. Publication No 2007/0141709 describes a general method for creating test solutions from aqueous MVS® stock solutions and core calculation procedures correspond to those described in U.S. Pat. Nos. 6,741,365 and 7,187,455. The aqueous-based solutions offered in the existing versions of the MVS® system meet the needs of many users, and the method for creating test solutions from non-aqueous solvents described in Publication No. 2007/0141709 also offers a test method needed by many users.

However, there are limitations to the MVS® system and to the method of Publication No. 2007/0141709. For example, there are limitations to the types of solvents that may be used to create test solutions from MVS® stock solutions while still maintaining accurate calculations following the mathematical approaches described in U.S. Pat. Nos. 6,741,365 and 7,187,455. Namely, any solvent that significantly alters the solution meniscus in the microtiter well can have a detrimental effect on the results calculated by said approaches. The MVS® methods described in U.S. Pat. Nos. 6,741,365 and 7,187,455 are based on a generally flat meniscus, a controlled or known solution chemistry that yields a reproducible meniscus, and/or a correction factor which accounts for minor deviations in meniscus shape.

When an uncharacterized solvent included in a new test solution from MVS® stock solutions (as described in Publication No. 2007/0141709) and the existing MVS® methods (as described in U.S. Pat. Nos. 6,741,365 and 7,187,455) are applied, there can be substantial errors, depending on how curved the meniscus becomes. The existing MVS® methods rely upon knowledge of this meniscus curvature in order to accurately return results on the volume delivered to the microtiter well, and can only do so through application of a correction factor. Thus, for solvents that have not been characterized for their affect on the solution meniscus, the results produced by the existing MVS® methods are less accurate than they could be. A method to cancel out the impact of variations in meniscus would be useful in determining the volume of a solution dispensed.

Various types of assays performed in life science and pharmaceutical laboratories require wash steps to remove unwanted or used reagents from a reaction vessel. For example, Enzyme-linked Immunosorbent Assays ("ELISA assays") require introduction of a tagged ligand. This tagged ligand binds to the molecular entity of interest, if it is present, and can be measured. The measurement is often a fluorometric, photometric or radiometric measurement, depending on the type of tag used. However, before the measurement step can occur, all unbound tagged-ligand must be removed from the reaction vessel by a rinse, or wash, step with a wash solution, often consisting of buffered water.

For assays conducted in microtiter plates, wash steps are commonly employed to exchange the solution within the wells. These wash steps are carried out using specialized equipment, called plate washers. Some examples of plate washers include the Tecan Power Washer 384 (Tecan US, Durham, N.C.) and the Biotek ELx405 Microplate Washer (BioTek Instruments, Winooski, Vt.).

Plate washers typically operate by dispensing a wash solution into the wells of the microtiter plate, while at the same time removing solution. Thus, they incorporate a dispense tube, and an aspirate tube, often side-by-side. The solution is thus flowed into and out of the well at a high velocity in order to effectively flush out unwanted reagents. The wash solution is dispensed into the wells by the dispense tip, which is connected by tubing to a large volume reservoir (often greater than 1 L) containing clean wash solution. The aspirate tip is connected via tubing to a waste reservoir. The dispense tip is often inserted into the well near the bottom, thus introducing wash solution at the bottom of the well. Conversely, the aspirate tip is inserted at a height near the top ⅓ of the well height. Positioning the aspirate tip at this height forces the well contents to be pushed by the wash solution, flowing into the well near the bottom, up towards the top of the well where it is removed by the aspiration tip. When the wash procedure is complete, the total solution height is equal to the height of the aspirate tip with respect to (or above) the plate bottom. This height thus determines the total volume of solution that will be left behind in the well.

For many microtiter plate-based assays incorporating a wash step, a quantitative understanding of the efficiency of washing is not needed. However, under some circumstances an understanding of how efficiently reagents are being removed from the wells by the plate washer is needed. One way to measure washing efficiency is to determine the degree of dilution that has occurred for the reagents in the wells. For such testing, the dilution testing scheme taught by existing methods can be used. However these existing methods require the use of a diluent solution to be added to the wash reservoir. In many cases, adding such a large volume of diluent is inconvenient and costly, especially considering a dead volume needed to fill the lines of 200-500 mL. Thus, an improved method for testing plate washing efficiency is desired.

Many test procedures carried out in life science and pharmaceutical laboratories also require dilution-based volume transfer steps, such as dose response and detection limit assays, for example. For many of these procedures, quantitative measurements are collected and decisions are made based upon an assumed, rather than a measured, dilution ratio. Often these assumptions are based upon a potentially misplaced trust in the performance of automated liquid delivery equipment. Accurately knowing sample concentration is critical for properly interpreting the experimental results, which can only be obtained if the experimental dilution ratio is known and controlled. Thus, the ability to accurately measure each dilution step in a dilution procedure having a plurality of dilution steps is required for proper assay analysis.

What is needed is a method that enables accurate calculation of the volume of a solution dispensed independent of meniscus. What is also needed is an effective method to determine the efficiency of plate washing routines. Further, what is needed is a method to determine dilution accuracy in a dilution procedure including a plurality of dilution steps.

SUMMARY OF THE INVENTION

It is an object of the present invention to provide a method and related system to enable accurate calculation of the volume of a solution dispensed independent of meniscus. It is also an object of the present invention to provide a system and related method to determine the efficiency of plate washing routines. Further, it is an object of the present invention to provide a system and related method to determine dilution accuracy in a dilution procedure including a plurality of dilution steps.

The first method of the present invention is a dual-dye photometric method providing results that are independent of meniscus shape, and can thus be used for uncharacterized solvent types. Thus, this new method is more widely applicable for volume testing of various solvents. In the method, a quantity of diluent is first used to determine a pathlength of light therethrough. It alone is used to account for meniscus shape in a vessel. A solution under test is then added to the vessel and mixed with the diluent. The solution can be of a solvent type which creates an unknown affect on the meniscus of the mixture but its volume calculation will not be affected by the meniscus shape. Hence, this procedure provides an option for testing a wider range of solvent types than the procedure described in U.S. application Ser. No. 11/305,301.

The second method of the present invention also involves a dual-dye photometric process providing results indicating plate washing efficiency. In this method, a solution contains a known concentration of a first chromophore (sometimes referred to herein as a dye) at a very high concentration that absorbs light at a first wavelength, but does not require another chromophore, and a diluent contains a known concentration of a second chromophore that absorbs light at a second wavelength. The method involves dispensing the diluent into a vessel such that the volume of the diluent is larger than would be left behind by a plate washer. The plate washer is then used to aspirate and remove the volume of diluent to the point that the diluent height equals an aspirate tip height of the washer. The absorbance of the diluent is then measured and used to determine a pathlength of light corresponding to the diluent height in the vessel. That information is then used to determine the dilutive effect of a plate washing instrument on the solution with the first chromophore.

The third method is a dual-dye photometric method for accurately determining each dilution step of a multi-step dilution process. This method is based upon conducting the desired dilution procedure by dispensing a solution into a vessel and mixing it with a diluent, wherein the solution includes a first chromophore and a second chromophore and the diluent includes only the second chromophore. Photometric measurements at made two different wavelengths. The measurements provided by this method are traceable to NIST for single or multiple point dilutions, and cover a testable dilution range of up to 1/2000. While this approach is similar to the standard dual-dye MVS® method described in U.S. Pat. No. 6,741,365, it provides a more precise approach for determining the degree of dilution experienced by dispensing one solution into a second solution, and allows for more accurate calculation of analyte concentrations throughout a multiple point dilution scheme.

In one embodiment of the present invention, a method includes the steps of: (1) adding to the vessel a diluent including a known concentration of a diluent chromophore which absorbs light at a second wavelength; (2) measuring the absorbance of the diluent chromophore at the second wavelength; (3) adding a volume of the sample solution to the vessel, wherein the sample solution includes a known concentration of a sample solution chromophore which absorbs light at a first wavelength, and wherein the sample solution does not include the diluent chromophore; (4) mixing the diluent and the sample solution in the vessel to produce a mixture of the sample solution and the diluent; (5) measuring the absorbance of the mixture of the sample solution and the diluent at the first wavelength and at the second wavelength; and (6) calculating the volume of the sample solution added to the vessel based on the measured absorbances at the first wavelength and the second wavelength. The step of calculating the volume of the sample solution also may include the steps of first calculating the volume of the diluent added to the vessel based on the absorbance per pathlength of the diluent at the second wavelength, the pathlength of light through the diluent as determined using the measured absorbance of the diluent chromophore at the second wavelength prior to adding the sample solution to the vessel, and the dimensions of the vessel. Further, the step of calculating the volume of the sample solution added to the vessel also may include a correction factor which accounts for a change in molar absorptivity.

In another embodiment of the invention, a method is provided that includes the steps of: (1) measuring in the sample solution the absorbance of the first chromophore at the first wavelength and the absorbance of the second chromophore at the second wavelength while the sample solution is contained in a first vessel of the plurality of vessels; (2) transferring a target volume of the sample solution from the first vessel to a second vessel of the plurality of vessels; (3) mixing into the sample solution in the second vessel a target volume of a diluent, wherein the diluent includes the second chromophore at a concentration substantially equivalent to the concentration of the second chromophore in the sample solution; (4) measuring the absorbance of the first chromophore at the first wavelength and the absorbance of the second chromophore at the second wavelength in the second vessel; and (5) calculating a dilution ratio for the sample solution contained in the second vessel, wherein the dilution ratio represents the extent to which the sample solution has been diluted by the diluent mixed into the second vessel. The method may further include the steps of: (1) transferring a target volume of the mixture in the second vessel to a third vessel of the plurality of vessels; (2) mixing with the mixture in the third vessel a target volume of the diluent; (3) measuring the absorbance of the first chromophore at the first wavelength and the absorbance of the second chromophore at the second wavelength in the third vessel; and (4) calculating a dilution ratio for the mixture of the sample solution and the diluent contained in the third vessel, wherein the dilution ratio represents the extent to which the mixture of the sample solution and the diluent has been diluted by the diluent mixed into the third vessel.

The method may optionally include the steps of: (1) repeating X more times the steps of i) transferring the mixture of the sample solution and the diluent, ii) mixing in the diluent, and iii) measuring the absorbances, wherein X is $\geq 1$, such that the last vessel of the plurality of vessels with the mixture of the sample solution and the diluent and the added diluent is vessel n and a preceding vessel is vessel m; and (2) calculating a dilution ratio for the mixture of the sample solution and the diluent contained in vessel n, wherein the dilution ratio represents the extent to which the mixture of the sample solution and the diluent has been diluted by the diluent mixed into vessel n.

In yet another embodiment of the present invention, a method is provided that includes the steps of: (1) transferring a target volume of the sample solution from a source into a vessel; (2) mixing into the sample solution in the vessel a target volume of the diluent, wherein the diluent includes the second chromophore at a concentration substantially equivalent to the known concentration of the second chromophore in the sample solution; (3) measuring the absorbance of the first chromophore at the first wavelength and the absorbance of the second chromophore at the second wavelength in the vessel; and (4) calculating a dilution ratio of the sample solution from the source, wherein the dilution ratio represents the extent to which the sample solution of the source has been diluted by the diluent mixed into the vessel. This method may include the steps of: (1) transferring a target volume of the mixture of the sample solution and the diluent from the vessel to a second vessel; (2) mixing a target volume of the diluent into the second vessel, wherein the diluent includes the second chromophore at a concentration substantially equivalent to the known concentration of the second chromophore in the sample solution; (3) measuring the absorbance of the first chromophore at the first wavelength and the absorbance of the second chromophore at the second wavelength in the second vessel; and (4) calculating a dilution ratio of the sample solution from the source, wherein the dilution ratio represents the extent to which the sample solution of the source has been diluted by the diluent through all mixing steps.

The third embodiment of the present invention optionally may even further include the optional steps of: (1) repeating X more times the steps of i) transferring the mixture of the sample solution and the diluent, ii) adding the diluent with the known concentration of the second chromophore to the mixture of the sample solution and the diluent and iii) measuring the absorbances, wherein X is $\geq 1$, such that any vessel but the source is vessel m and the source is represented as vessel 0; and (2) calculating a dilution ratio for the sample solution from the source, wherein the dilution ratio represents the extent to which the sample solution of the source has been diluted by the diluent through all mixing steps.

In a fourth embodiment of the present invention, a method is provided that includes the steps of: (1) adding to a first vessel of a first set of a plurality of vessels a target volume of a first sample solution, wherein the first sample solution includes a first known concentration of the first chromophore and a known concentration of the second chromophore; (2) adding to a first vessel of a second set of the plurality of vessels a target volume of a second sample solution including a second known concentration of the first chromophore and the known concentration of the second chromophore, wherein the second known concentration of the first chromophore of the second sample solution is higher than the first known concentration of the first chromophore of the first sample solution, and wherein the target volume of the second sample solution added to the first vessel of the second set is substantially equivalent to the target volume of the first sample solution added to the first vessel of the first set; (3) carrying out a first dilution protocol step comprising: (i) mixing into the first vessel of the first set a first target volume of a diluent, wherein the diluent includes the second chromophore at a concentration substantially equivalent to the known concentration of the second chromophore in the first sample solution and the second sample solution; (ii) mixing into the first vessel of the second set the first target volume of the diluent; and (iii) measuring the absorbance of the first chromophore at the first wavelength and the absorbance of the second chromophore at the second wavelength in the first vessel of the first set; (4) carrying out a second dilution protocol step comprising: (i) transferring a target volume of the mixture of the first sample solution and the diluent of the first vessel of the first set to a second vessel of the first set; (ii) mixing a second target volume of the diluent into the second vessel of the first set; (iii) transferring a target volume of the mixture of the second sample solution and the diluent of the first vessel of the second set to a second vessel of the second set; (iv) mixing the second target volume of the diluent into the second vessel of the second set; and (v) measuring the absorbance of the first chromophore at the first wavelength and the absorbance of the second chromophore at the second wavelength in the second vessel of the second set; and (5) calculating a dilution ratio of the dilution protocol based on the absorbance measurements made in steps 3.iii and 4.v, wherein the dilution ratio represents the extent of dilution occurring between the first dilution protocol step and the second dilution protocol step.

In a fifth embodiment of the present invention, a method is provided that includes the steps of: (1) placing a diluent in a first vessel to a level establishing a diluent height, wherein the diluent includes a known concentration of a diluent chromophore that absorbs light at a second wavelength, and wherein the first vessel has known dimensions; (2) measuring the absorbance of the diluent chromophore in the first vessel at the second wavelength; (3) calculating the pathlength of light through the diluent in the first vessel based on the measured absorbance of the diluent chromophore and a known absorbance per pathlength of the diluent chromophore, wherein the pathlength of light through the diluent is equal to the diluent height; (4) adding to a second vessel a target volume of a sample solution, wherein the sample solution includes a known concentration of a sample solution chromophore that absorbs light at a first wavelength, wherein dimensions of the second vessel are substantially equivalent to the known dimensions of the first vessel; (5) adding a wash solution to the second vessel and removing at least some of a mixture of the wash solution and the sample solution from the second vessel to establish a mixture height in the second vessel, wherein the mixture height is substantially equivalent to the diluent height; (6) measuring the absorbance of the sample solution chromophore in the second vessel at the first wavelength; and (7) calculating a dilution ratio for the sample solution contained in the second vessel, wherein the dilution ratio represents the extent to which the sample solution has been diluted by the wash solution added into the second vessel. The method includes the option to carry out the step of adding wash solution to the second vessel and removing at least some of the wash solution and the sample solution from the second vessel a plurality of times before the step of measuring the absorbance of the sample solution chromophore. Alternatively, the steps of i) adding wash solution to the second vessel and removing at least some of the wash solution and the sample solution from the second vessel and ii) measuring the absorbance of the sample solution chromophore may be carried out a plurality of times in succession.

These and other features and advantages of the invention will be apparent upon review of the following detailed description, appended drawings and accompanying claims.

BRIEF DESCRIPTION OF THE DRAWINGS

FIG. 1 is a table showing the approximate dilution range measurable by each one of the five MVS® Sample Solutions of Example One, Example Two and Example Three of the present invention described herein.

FIG. 2 is a table showing the experimental design which defines the contents added to each column of a microtiter plate of Example One of the present invention described herein.

FIG. 3 is a table showing an experimental demonstration of Example One of the present invention described herein.

FIG. 4 is a table showing data obtained by carrying out Example Two of the present invention described herein.

FIG. 5 is a table showing two stepwise dilution calculations of Example Three of the present invention described herein.

DETAILED DESCRIPTION OF THE PREFERRED EMBODIMENTS OF THE INVENTION

The present invention is a method and related system for determining the impact of diluting a solution, either to accurately measure the volume of the solution dispensed, or to accurately measure the amount of dilution that has occurred. In a first system embodiment of the present invention includes the following components: (1) a microtiter plate having a plurality of wells, wherein each well has a shape of known geometrical dimensions, (2) a microtiter plate reader for measuring absorbance values of liquids dispensed into the wells of the microtiter plate, (3) sample solutions containing variable, but known concentrations of a first chromophore which absorbs light at a first wavelength (herein referred to as "$\lambda_1$"), (4) a diluent solution containing a known, fixed concentration of a second chromophore which absorbs light at a second wavelength (herein referred to as "$\lambda_2$"), and (5) a mixing device. It is to be understood, however, that the system is not limited to having these components. Therefore, the system may have more or fewer components, and other components may be substituted for any or all of these components of this first embodiment. Examples of suitable systems are described in the incorporated references.

A first primary method embodiment of the present invention includes the steps of 1) adding a diluent to a well of a microtiter plate, wherein the well has a shape of known geometrical dimensions; 2) measuring the absorbance of the second chromophore in the well at the second wavelength; 3) adding to the well a volume of sample solution, wherein the sample solution includes a concentration of a sample solution chromophore which absorbs light at a first wavelength; 4) mixing the diluent and the sample solution in the well to produce a mixture of the sample solution and the diluent; 5) measuring the absorbance of the mixture of the sample solution and the diluent at the first wavelength and at the second wavelength; and 6) calculating the volume of the sample solution added to the well.

The core mathematical model upon which the method of the present invention is based is the Beer-Lambert law. Simply stated, the law claims that when light is passed through a solution containing some concentration of chromophore (i.e., dye), the amount of light absorbed by that dye solution is proportional to both the concentration of the chromophore and the interaction pathlength of the light with the dye solution. In mathematical terms, the law is written as:

$$A_\lambda = \epsilon_\lambda l C \quad (1)$$

where $A_\lambda$ is the absorbance of the chromophore at a specific wavelength $\lambda$, $\epsilon_\lambda$ is a physical constant of the chromophore at wavelength $\lambda$ known as the molar absorptivity, l is the pathlength of light through the dye solution, and C is the molar concentration of the chromophore in the dye solution. This proportionality is most commonly used to determine an unknown concentration of a chromophore in a dye solution, where the molar absorptivity at the measurement wavelength is known and the pathlength of light through the dye solution is known or fixed.

Alternatively, Equation (1) also states that the measured absorbance is proportional to the pathlength of light through the dye solution. If both the molar absorptivity and concentration of the chromophore in a dye solution are known, then Equation (1) can be used to determine an unknown pathlength traversed by a photometric light beam. To use the Beer-Lambert law in this way it becomes convenient to combine the molar absorptivity ($\epsilon_\lambda$) and concentration (C) terms:

$$\epsilon_\lambda C = a_\lambda \quad (2)$$

where the new term $a_\lambda$ represents the absorbance of the dye solution per unit pathlength at the wavelength $\lambda$. Substitution of this new term into Equation (1) gives:

$$A_\lambda = a_\lambda l \quad (3)$$

Equation (3) is the basic form of the Beer-Lambert law that is used for the method of the present invention.

As noted, the first step of the first primary method involves adding a volume of diluent ($V_d$) into a well. The volume of diluent is chosen so that the total volume of sample solution (to be later added to the well) and diluent does not exceed a defined working volume within the well of the chosen plate type. For example, the defined working volume used for each well of some 96-well microtiter plates is 200 µL, whereas the working volume for each well of some 384-well plates is only 55 µL.

After dispensing the diluent, orbital mixing may be employed to ensure sufficient spreading of the diluent across the bottom surface of the well, and flattening of the meniscus. This spreading may be achieved, for example, by using the mixing device of the apparatus of the present invention to agitate the mixture. If the sample solution under test does not allow for a flat meniscus, then the curvature of the meniscus must be characterized. Also, because an absorbance measurement will be made of the dispensed diluent, spreading across the entire well bottom is required, otherwise a quantitative absorbance measurement will not be achieved. In practice this means that a lower limit must also be placed on the amount of the diluent volume used. For a 96-well plate, this lower limit is ~50 µL.

After mixing, the absorbance at $\lambda_2$ (referred to as "$A_{\lambda 2}$") is measured for all wells containing diluent. Because the diluent contains a known concentration of the second chromophore, Equation (2) can be used to characterize the absorbance per pathlength of the diluent at $\lambda_2$ (referred to as "$a_d$"). Thus, by incorporating the known $a_d$ for the diluent and the measured absorbance $A_{\lambda 2}$ into Equation (3), the pathlength of light through the diluent ($l_d$) can be determined by using the Equation:

$$l_d = A_{\lambda 2} / a_d \qquad (4)$$

By combining $l_d$ with the known geometrical dimensions of the microtiter wells, the volume of diluent in each well can be calculated. The exact equation used to determine the total diluent volume ($V_d$) is dependent upon the shape of the wells of the particular microtiter plate used. For commonly used round-well, flat-bottom plates, $V_d$ is modeled as an inverted, truncated cone:

$$V_d = \pi l_d \frac{D^2}{4} + \pi D l_d^2 \frac{\tan\theta}{2} + \pi l_d^3 \frac{\tan^2\theta}{3} \qquad (5)$$

where D is the diameter of the bottom of the microtiter well, and $\theta$ is the taper angle of the sidewall. Similar expressions (not given here) for determining $V_d$ can be used when square-well microtiter plates are implemented.

Once the diluent volume $V_d$ has been determined, a sample solution volume, $V_s$, is dispensed into the wells containing diluent. As with the diluent, the sample solution possesses a characteristic absorbance per pathlength at $\lambda_1$ (referred to as "$a_s$") based on the known concentration of the first chromophore, as expressed in Equation (2). It should be noted again that in the first embodiment of the method, the sample solution contains only the first chromophore and none of the second chromophore.

After dispensing the sample solution into the wells containing diluent, the plate preferably is mixed until a homogenous mixture of sample and diluent has been achieved, and absorbance measurements are then made at both $\lambda_1$ and $\lambda_2$. The total volume of the combination of the sample solution and diluent in any particular well is given by:

$$V_T = V_d + V_s \qquad (6)$$

Because each one of the sample solution and the diluent contains only one chromophore, and because the concentration of each chromophore is known for each one of the sample solution and the diluent prior to their mixing, Equation (3) can be used to express the measured absorbance values at each wavelength, $\lambda_1$ and $\lambda_2$, for the mixture:

$$A_{\lambda 1} = a_s l \cdot \left(\frac{V_s}{V_T}\right) \qquad (7)$$

$$A_{\lambda 2} = a_d l \cdot \left(\frac{V_d}{V_T}\right) \qquad (8)$$

where l refers to the total pathlength of light through the homogenous mixture of sample solution and diluent, and the terms ($V_s/V_T$) and ($V_d/V_T$) correspond to the dilution ratios experienced by the sample solution and the diluent, respectively.

It is important to note that the total pathlength l may depend on either or both of the meniscus shape and the total solution volume $V_T$. However, if a ratio of the absorbance values is calculated, the value calculated is independent of both l and $V_T$. Dividing Equation (7) by Equation (8) results in removal of both l and $V_T$ terms as expressed by:

$$\frac{A_{\lambda 1}}{A_{\lambda 2}} = \frac{a_s}{a_d} \cdot \frac{V_s}{V_d} \qquad (9)$$

Solving Equation (9) for the sample volume $V_s$ gives:

$$V_s = V_d \cdot \frac{a_d}{a_s} \cdot \frac{A_{\lambda 1}}{A_{\lambda 2}} \qquad (10)$$

Because the diluent volume is determined in a separate step, it is the only measurement whose meniscus shape is important to account for. In other words, the diluent solution will need to have a relatively flat meniscus when dispensed into the wells of a microtiter plate, or at least have a controlled, reproducible meniscus that will allow for sufficient correction. Such a correction is needed because the meniscus curvature causes the solution to no longer conform to the ideal geometrical shape of the well. In other words, the solution pathlength measured photometrically no longer conforms to the height of the ideal well shape, but is either too short (for concave meniscus curvature) or too long (for convex meniscus curvature). A correction for such meniscus curvature could be performed by determining the volume of diluent in the wells using a gravimetric approach, then determining the volume using the photometric approach. A correction factor can then be determined as the difference between the gravimetric volume and the photometric volume as a function of total solution pathlength in the well. Another possible approach for correcting for meniscus curvature would be to determine the actual radius of curvature and then calculate the enclosed volume of the geometrical shape defined by the well dimensions and the meniscus curvature.

In the first primary method embodiment of the invention, the sample solution can be a solvent which creates an unknown affect on the meniscus of the mixture of the sample solution and the diluent. While the meniscus curvature is accounted for when the diluent volume is measured, the sample volume calculation will not be affected by the meniscus shape as demonstrated by Equation (10).

While the first primary method embodiment is applicable to various sample solvent types that may cause an uncharacterized change to the meniscus, it does not account for other interfering properties that might be created by the solvent of interest. For example, the sample solution under test may contain some concentration of analyte that either absorbs and/or scatters light at either or both $\lambda_1$ and $\lambda_2$. Under such circumstances, a blank solution containing the same concentration of the interfering analyte as present in the total volume $V_T$ may be prepared and used to collect a zero reading at both of those wavelengths. When the blank solution is used in this manner, this zero reading may then be subtracted from all raw absorbance measurements collected at each wavelength before use in Equation (10). Those of ordinary skill in the art would recognize that such practice is commonly used for photometric measurements.

In some cases, the first primary method embodiment may be affected by chemical or physical changes that a solvent of interest imparts on the either or both of the chromophores of the mixture of sample solution and the diluent. For example, some solvent types may cause precipitation of either or both chromophores. In this case, different chromophores that are soluble in the solvent of interest would have to be used. In another example, the solvent of interest may cause a change to the characterized molar absorptivity ($\epsilon$) of either or both chromophores. Overcoming this physical spectral change would require characterization of the magnitude of the imparted change, from which a correction could be made to the measured absorbance values used in Equation (10).

As discussed below, a quantitative measurement of the efficiency of plate washing can be achieved by determining the degree of dilution of reagents. Existing dilution methods and the third primary embodiment of the method of the present invention described herein can be used to achieve this goal if the user is willing to consume several hundred milliliters of diluent solution. The volume of solution required to fill the dispense tubing is often 200-500 mL, and each wash step can require approximately 150-250 mL per plate. This is a significant volume that many users may not be willing to use, however.

A second primary method embodiment of the present invention allows the user to avoid the need of having to fill the wash reservoir with diluent. This second embodiment involves the use of two different chromophore (dye) solutions. A first dye solution (e.g., a "red" dye solution) contains a known concentration of a first chromophore at a very high concentration that absorbs light at a first wavelength ($\lambda_1$), but does not include any other chromophore. A second dye solution (e.g., a "blue" dye solution) contains a known concentration of a second chromophore that absorbs light at a second wavelength ($\lambda_2$). Whereas the first dye solution contains a high concentration of the first chromophore, which has an immeasurable absorbance in its concentrated form, the second dye contains a known concentration of the second chromophore at a spectrophotometrically measurable absorbance. The sample solutions and diluent previously described for the first primary method embodiment have the requisite properties for this approach, and will be used to further describe the second primary method embodiment of the invention. Because the concentration of each chromophore is known for each of the diluent and the sample solution, both the diluent and the sample solution can be characterized by the absorbance per pathlength values as expressed in Equation (2). The absorbance per pathlength for the sample solution at the first chromophore ($a_s$), as well as for the diluent at the second chromophore ($a_d$) are known and given by:

$$a_s = \epsilon_{\lambda 1} \cdot C_{\lambda 1} \quad (11)$$

$$a_d = \epsilon_{\lambda 2} \cdot C_{\lambda 2} \quad (12)$$

where $\lambda 1$ and $\lambda 2$ are used to denote the first chromophore at the first wavelength and the second chromophore at the second wavelength, respectively.

The second primary method embodiment involves dispensing the diluent using a liquid handling apparatus (e.g., handheld pipette, automated liquid handler, etc.), containing the known concentration of the second chromophore into the wells of the microtiter plate. In the second primary method embodiment, the volume of the diluent is larger than would be left behind by the plate washer, meaning that the solution height is higher than the height of the aspirate tip of the plate washer. The microtiter plate is then loaded onto the plate washer and the aspirate tips are inserted into the wells with the diluent. Because the diluent height is greater than the aspirate tip height, the aspirate tips are partially immersed into the diluent. The plate washer is then used to aspirate and remove the volume of diluent to the point that the solution height equals the aspirate tip height. At this point the microtiter plate is removed and inserted into a plate reader, and the absorbance of the diluent is measured at $\lambda_2$. From this step the total solution height can be measured. Equation (4) is used to measure the height of the diluent in the well ($l_d$), which is equal to the solution height that the plate washer will leave after a wash procedure.

A different microtiter plate is then filled with sample solution. This sample solution contains a known concentration of the first chromophore, and is characterized by the absorbance per pathlength value shown in Equation (11). Although any type of liquid dispensing apparatus may be used to fill the wells, the volume dispensed into the wells should be equal to the volume of solution that would normally be present during an assay. This is the step that should mimic the assay being tested. Thus, if the washing efficiency during an ELISA assay is being tested, for example, then the volume of sample placed in the wells should be the same as the solution volume that would be present when the plate is inserted into the plate washer for washing. The plate filled with the desired volume of sample solution is then inserted into the plate washer and the desired wash cycle is conducted. This wash cycle causes a dilution of the sample solution, and leaves behind a total solution volume with a liquid height equal to the height that was previously measured by the diluent test step ($l_d = l_{solution}$).

The diluted sample solution in the wells of the microtiter plate is then measured photometrically with a plate reader. This measurement gives an absorbance $A_s$ at $\lambda_1$ for the first chromophore in the sample solution. The absorbance per pathlength for this diluted sample solution ($a_{s,diluted}$) can then be calculated by:

$$a_{s,diluted} = \frac{A_s}{l_d} \quad (13)$$

where the solution pathlength $l_d$ is determined from the diluent filled plate.

Once the $a_{s,diluted}$ is determined, the plate washing efficiency can be assessed by determining the extent of dilution experienced by the sample solution. This extent of dilution can be calculated as a dilution ratio, which is determined by comparing to the known absorbance per pathlength of the neat, concentrated sample solution ($a_s$) to the absorbance per pathlength of the diluted sample solution ($a_{s,diluted}$) left in the well after the wash cycle, as expressed by:

$$R_{WE} = \frac{a_s}{a_{s,diluted}} \quad (14)$$

where $R_{WE}$ is the dilution ratio of the neat versus diluted sample solution, and is taken as a measure of the degree of washing efficiency of a plate washing cycle. ("Neat sample solution" is undiluted sample solution).

Equation (14) provides a way to determine the efficiency of plate washing by comparing the measured dilution ratio against a desired level of dilution. The ideal performance of a plate washer would result in complete removal of unwanted components. However, adequate performance would only require removal of unwanted reagents beyond some pre-determined threshold, which can be expressed in terms of a minimum dilution. The second embodiment of the method of the present invention allows for testing the plate washer against such a dilution threshold.

In an alternative system embodiment of the present invention, the system includes: 1) a microtiter plate having wells for holding liquid volumes, 2) a microtiter plate reader for measuring absorbance values of solutions dispensed into the wells of the microtiter plate, 3) sample solutions containing variable, but known concentrations of a first chromophore which absorbs light at $\lambda_1$, and a fixed, known concentration of a second chromophore which absorbs light at $\lambda_2$, 4) a diluent containing a known, fixed concentration of a second chromophore which absorbs light at $\lambda_2$, and 5) a microtiter plate mixing apparatus. It should be noted that a significant difference between the standard MVS® approach described in U.S. Pat. No. 6,741,365 and the method of the invention described herein is that the dimensions of the wells of the microtiter plate are not needed for the present method. This is a significant deviation from the standard MVS® approach as the plate dimensions are used in the volume calculations of the standard MVS® approach.

In a third primary method embodiment of the present invention, steps include: (1) transferring a target volume of the sample solution from a source into a vessel; (2) mixing into the sample solution in the vessel a target volume of the diluent, wherein the diluent includes the second chromophore at a concentration substantially equivalent to the known concentration of the second chromophore in the sample solution; (3) measuring the absorbance of the first chromophore at the first wavelength and the absorbance of the second chromophore at the second wavelength in the vessel; and (4) calculating a dilution ratio of the sample solution from the source, wherein the dilution ratio represents the extent to which the sample solution of the source has been diluted by the diluent mixed into the vessel. An object of the third primary method embodiment is to calculate the accuracy of each dilution step as compared to the defined target.

Similar to the first primary method embodiment, the core mathematical model upon which the third primary method embodiment is based is the Beer-Lambert law expressed in Equation (1). The concentration of each chromophore is known for each solution, and is defined for the first chromophore in the sample ($a_s$), and for the second chromophore in the diluent ($a_d$) by Equations (11) and (12). It should be noted that the concentration of the second chromophore in the sample solution is fixed to equal the concentration of the second chromophore in the diluent. Thus, the absorbance per pathlength for all solutions, both samples and diluent, at the second chromophore is fixed and can be expressed as $a_d$. In practice this means that mixtures of any ratio of sample solution to diluent will result in the same concentration of the second chromophore, but a varying concentration of the first chromophore. This in essence allows the second chromophore to be used as an internal standard.

The first step of the third primary method embodiment entails dispensing sample solution volume $V_{s1}$ into well 1, followed by removal of volume $V_{s2}$ from well 1 and dispensing it into well 2. The net volume of sample solution left in well 1 ($V_1$) is given by:

$$V_1 = V_{s1} - V_{s2} \tag{15}$$

Because the concentration of the first and second chromophores in well 1 are known, the depth of liquid ($l_1$) in well 1 can be determined by measuring the absorbance of the second chromophore and using Equation (3) above. More directly expressed, the depth of liquid is given by:

$$l_1 = \frac{A_{1,\lambda 2}}{a_d} \tag{16}$$

where $A_{1,\lambda 2}$ denotes the measured absorbance in well 1 at the second wavelength $\lambda_2$, and $a_d$ is the absorbance per pathlength of the second chromophore.

The Beer's law expression for the absorbance of the first chromophore in well 1 is given by:

$$A_{1,\lambda 1} = \epsilon_{\lambda 1} \cdot C_{1,\lambda 1} \cdot l_1 \tag{17}$$

where $C_{1,\lambda 1}$ is used to indicate the concentration in well 1 of the first chromophore. Substituting Equations (11) and (16) into (17) gives the following:

$$A_{1,\lambda 1} = A_{1,\lambda 2} \cdot \frac{a_s}{a_d} \tag{18}$$

A volume of diluent ($V_{d2}$) is then added to the sample solution volume ($V_{s2}$) already present in well 2. The sample solution and diluent are mixed until homogenous and a volume $V_{s3}$ of the mixture of sample solution and diluent is then removed and dispensed into well 3. The net volume in well 2 is given by:

$$V_2 = V_{s2} + V_{d2} - V_{s3} \tag{19}$$

Because the concentration of the second chromophore is fixed for all sample solutions and diluent, it is known for well 2 and the solution depth can be determined by the measured absorbance of the second chromophore at $\lambda_2$, as given by:

$$l_2 = \frac{A_{2,\lambda 2}}{a_d} \tag{20}$$

The concentration of the first chromophore in well 2 has been diluted and is given by:

$$C_{2,\lambda 1} = C_{1,\lambda 1} \cdot \left(\frac{V_{s2}}{V_{s2} + V_{d2}}\right) \tag{21}$$

where $$(V_{s2} / V_{s2} + V_{d2})$$

represents the dilution factor of the first chromophore in going from well 1 to well 2.

The Beer's law expression for the absorbance of the first chromophore in well 2 is given by:

$$A_{2,\lambda 1} = \epsilon_{\lambda 1} \cdot C_{2,\lambda 1} \cdot l_2 \tag{22}$$

Substitution of Equations (11), (20) and (21) into (22) gives the following reduced expression:

$$A_{2,\lambda 1} = A_{2,\lambda 2} \cdot \frac{a_s}{a_d} \cdot \left(\frac{V_{s2}}{V_{s2} + V_{d2}}\right) \tag{23}$$

A first a volume of diluent ($V_{d3}$) is then added to the mixture of sample solution and diluent volume ($V_{s3}$) present in well 3. The mixture of sample solution and diluent are mixed and a volume $V_{s4}$ is then removed and dispensed into well 4. As occurred for well 2, the expressions for the net volume and solution depth for well 3 are given as:

$$V_3 = V_{s3} + V_{d3} - V_{s4} \quad (24)$$

$$l_3 = \frac{A_{3,\lambda 2}}{a_d} \quad (25)$$

The concentration of the first chromophore in well 3 has been diluted by a ratio of $$(V_{s3} / V_{s3} + V_{d3})$$

and is given by:

$$C_{3,\lambda 1} = C_{2,\lambda 1} \cdot \left( \frac{V_{s3}}{V_{s3} + V_{d3}} \right) \quad (26)$$

Substitution of the expression for the concentration of the first chromophore in well 2 from Equation (21) into Equation (26) gives:

$$C_{3,\lambda 1} = C_{1,\lambda 1} \cdot \left( \frac{V_{s2}}{V_{s2} + V_{d2}} \right) \cdot \left( \frac{V_{s3}}{V_{s3} + V_{d3}} \right) \quad (27)$$

The Beer's law expression for the absorbance of the first chromophore in well 3 is given as:

$$A_{3,\lambda 1} = \epsilon_{\lambda 1} \cdot C_{3,\lambda 1} \cdot l_3 \quad (28)$$

Substitution of Equations (11), (26) and (27) into (28) gives the following reduced expression:

$$A_{3,\lambda 1} = A_{3,\lambda 2} \cdot \frac{a_s}{a_d} \cdot \left( \frac{V_{s2}}{V_{s2} + V_{d2}} \right) \cdot \left( \frac{V_{s3}}{V_{s3} + V_{d3}} \right) \quad (29)$$

The steps described above can be followed to develop expressions for continued analysis of well 4 and beyond.

An object of this analysis is to describe a method for calculating the dilution ratio of each step. The dilution ratio in going from well 1 to well 2 is defined as:

$$R_{12} \equiv \frac{C_{1,\lambda 1}}{C_{2,\lambda 1}} \quad (30)$$

Inserting the expression for the concentration of the first chromophore in well 2 from Equation (21) into Equation (30) gives the following expression:

$$R_{12} \equiv \frac{C_{1,\lambda 1}}{C_{1,\lambda 1} \cdot \left( \frac{V_{S2}}{V_{S2} + V_{D2}} \right)} = \left( \frac{V_{S2} + V_{D2}}{V_{S2}} \right) \quad (31)$$

The Beer's law expression for the absorbance ratio of the first chromophore in well 1 compared to well 2 is given through dividing Equation (18) by Equation (23):

$$\frac{A_{1,\lambda 1}}{A_{2,\lambda 1}} = \frac{\frac{a_s}{a_d} \cdot A_{1,\lambda 2}}{\frac{a_s}{a_d} \cdot A_{2,\lambda 2} \left( \frac{V_{S2}}{V_{S2} + V_{D2}} \right)} \quad (32)$$

Substituting Equation (31) and simplifying gives:

$$\frac{A_{1,\lambda 1}}{A_{2,\lambda 1}} = \frac{A_{1,\lambda 2}}{A_{2,\lambda 2}} \cdot R_{12} \quad (33)$$

Solving for the dilution ratio gives:

$$R_{12} = \frac{A_{1,\lambda 1}}{A_{2,\lambda 1}} \cdot \frac{A_{2,\lambda 2}}{A_{1,\lambda 2}} \quad (34)$$

Likewise, in going from well 2 to well 3, the dilution ratio is:

$$R_{23} = \frac{A_{2,\lambda 1}}{A_{3,\lambda 1}} \cdot \frac{A_{3,\lambda 2}}{A_{2,\lambda 2}} \quad (35)$$

A more general expression for dilution steps is given as:

$$R_{mn} = \frac{A_{m,\lambda 1}}{A_{n,\lambda 1}} \cdot \frac{A_{n,\lambda 2}}{A_{m,\lambda 2}} \quad (36)$$

The analysis described above demonstrates that the dilution ratios for each well can be determined by measuring the absorbance ratios of the first and second chromophores for each well. It is important to note that neither the dye concentration nor the well dimensions are required for this analysis. As demonstrated by Equation (36), the only quantities needed to calculate a dilution ratio in going from one well to another are the measured absorbance values for both the first and second chromophores. Also, this analysis is independent of meniscus shape, so long as the meniscus curvature is not significantly different between well m and well n. The only limitation for the stepwise analysis of dilution testing described by Equation (36) is that the absorbance values for both chromophores have to be in a measurable absorbance range for the spectrophotometer used. In other words, for this dilution calculation to be valid, the absorbance of both the first and second chromophores have to be in the linear, Beer's law absorbance range in both well m and well n.

As discussed, Equation (36) allows for calculating the degree of dilution between any two dilution steps in a series of dilutions of a protocol, but only if the absorbance values for both chromophores is in a measurable range in both wells. This requirement can pose a significant limitation for commonly used dilution protocols which cover greater than a 1,000 fold dilution between the start and end wells. The above approach provides a method for overcoming such a limitation, so long as the starting concentrations for both chromophores are known. For example, assume that the dilution ratio in going from well 1 to well 3 is to be determined. Such a dilution is expressed as:

$$R_{13} = R_{12} \cdot R_{23} = \left(\frac{A_{1,\lambda 1}}{A_{2,\lambda 1}} \cdot \frac{A_{2,\lambda 2}}{A_{1,\lambda 2}}\right) \cdot \left(\frac{A_{2,\lambda 1}}{A_{3,\lambda 1}} \cdot \frac{A_{3,\lambda 2}}{A_{2,\lambda 2}}\right) \quad (37)$$

Simplifying Equation (37) demonstrates that the dilution step between well 1 and well 3 can be calculated directly, without any measurements of well 2:

$$R_{13} = \frac{A_{1,\lambda 1}}{A_{3,\lambda 1}} \cdot \frac{A_{3,\lambda 2}}{A_{1,\lambda 2}} \quad (38)$$

Because the contents of well 1 are defined, Equation (18) can be incorporated into Equation (38) to give:

$$R_{13} = \frac{a_s}{a_d} \cdot \frac{A_{3,\lambda 2}}{A_{3,\lambda 1}} \quad (39)$$

This can be more generally stated as:

$$R_{0m} = \frac{a_s}{a_d} \cdot \frac{A_{m,\lambda 2}}{A_{m,\lambda 1}} \quad (40)$$

where $R_{0m}$ refers to the dilution experienced by a starting solution with known concentrations of both the first and second chromophores that is dispensed into well m which contains diluent. This dilution calculation can be applied between two wells where the first well contains a known concentration of both chromophores, and the second well contains a dilution that results in measurable absorbance values for both the first and second chromophores.

For the case where the concentrated solution is contained in well 1, Equation (40) is used to calculate the dilution ratio in going from well 1 to well m, where well 1 contains neat sample solution. For very large dilution steps, it may be required to start with a highly concentrated chromophore solution which is beyond the measurable absorbance range of the plate reader in order to have a measurable concentration of chromophore in well m. Such a dilution step is still measurable so long as the concentrations of both the first and second chromophores are known for this solution. Thus, Equation (40) provides the means to calculate accuracy of very large dilution steps.

Equations (36) and (40) demonstrate how the third primary method embodiment is used to measure two different types of dilution step. Equation (36) can be used to measure smaller dilution steps that result in measurable absorbance values in both wells m and n, where the solution has been diluted from well m into well n. Equation (40) is for determining large step dilutions where the starting solution is neat sample solution. In the case of Equation (40), the absorbance obtained from well m is used, along with the absorbance per pathlength values for the neat sample solution.

Another type of dilution protocol step to be considered in use of the third primary method is one that entails a multi-step procedure where the absorbance of either well m or well n is immeasurable. Equation (40) allows for calculating the dilution ratio for the first step of such a protocol by starting with a sample solution with a known absorbance per pathlength value for both dyes. By selecting a sample solution with an appropriate concentration, the first dilution step will produce a diluted solution with a measurable absorbance at both 520 nm and 730 nm, and Equation (40) will accurately calculate the dilution that has occurred. However, suppose that the dilution procedure then required a second large dilution step that resulted in a red dye absorbance that was too small to measure. The way in which this second dilution step is assessed is by repeating the dilution method in a different microtiter plate, but starting with a more concentrated sample solution. Data from both plates can then be used to determine the dilution step that has occurred in going from well m into well n, as defined by:

$$R_{m_i n_j} = \frac{\left(\frac{a_{s_j}}{a_{d_j}}\right) \cdot \left(\frac{A_{n_j,\lambda 2}}{A_{n_j,\lambda 1}}\right)}{\left(\frac{a_{s_i}}{a_{d_i}}\right) \cdot \left(\frac{A_{m_i,\lambda 2}}{A_{m_i,\lambda 1}}\right)} \quad (41)$$

where $R_{m_i n_j}$ refers to the dilution that has occurred between well m and well n for the dilution protocol that was performed, where the data for well m is taken from plate i, and the data for well n is taken from plate j. To use Equation (41), the same dilution protocol is conducted for two different plates: 1) plate i using a sample solution that results in a measurable absorbance in well m, and 2) plate j using a different, more concentrated sample solution that results in a measurable absorbance in well n. It is instructive to note that Equation (41) is the quotient of the dilution calculations from Equation (40) for well m in plate i and well n in plate j.

By using the dual-dye, dual-wavelength method described above, dilution ratios for all steps of a dilution scheme can be measured using Equations (36), (40) and (41). Not all dilutions will be within the measurable range of the plate reader, however. To overcome this limitation, the initial concentrations of the chromophores in solution will need to characterized and known. Also, for multi-step dilutions, one starting solution may not be capable of covering all dilution steps. For such a scenario, different starting solutions with different starting concentrations will need to be dispensed following the multiple steps of the dilution protocol. While one starting solution may not result in measurable absorbance values beyond the first few steps, another starting solution may not provide measurable absorbance values until after multiple steps in the dilution scheme have already been made. Thus, if the dilution method is followed using different starting solutions, the accuracy of each step can be determined.

To fully understand the accuracy of each step in a multi-step dilution protocol, one must consider the measurable absorbance range of the sample solutions used. For example, consider a four-step serial dilution protocol where each step consists of a 1:4 dilution. Assuming a starting concentration of a first chromophore that yields an absorbance of 2.5, which is within the measurable absorbance range of most spectrophotometers, Equation (1) shows that the absorbance will be reduced by a factor of 1/64 after the third dilution, which corresponds to an absorbance value of 0.039. While such a small absorbance is measurable by many spectrophotometers, the noise component of such a small value can be significant. Thus, the sample solution used in this case provides measurable quantities only for the first two dilution steps of this protocol. Now assume that the protocol is repeated for a more concentrated sample solution whose first chromophore concentration would yield an equivalent absorbance of 75, if such a measurement were achievable by a spectrophotometer. The absorbance of the first chromophore would still be beyond measurement after the first and second dilution steps. However, the absorbance of the third (1:64)

and fourth (1:256) dilution steps would be 1.17 and 0.29, respectively. Thus, the protocol is conducted two separate times, one using the sample solution with an initial absorbance of 2.5 for the first chromophore, the second using the more concentrated sample solution with an initial absorbance of 75 for the first chromophore. By using these two different sample solutions with different concentrations of the first chromophore, and repeating the dilution protocol for each solution, all four steps of the 1:4 serial dilution protocol can be assessed using Equations (36), (40) and (41), assuming that the first chromophore absorbance per pathlength values ($a_s$) can be determined for each starting sample solution.

The third primary method embodiment of the present invention is more specifically described with reference to three Examples; however, it is not to be construed as being limited thereto.

Example ONE

The process of Example One was carried out for the purpose of determining the dispense accuracy of a liquid handling device, which specifically was a Rainin, 20-200 µL LTS multichannel pipette.

The process of Example One included the use of a plurality of MVS® Diluent and Sample Solutions (i.e., "Range A", "Range B", "Range C", "Range D" and "Range E" sample Solutions), which are commercially available from Artel, Inc. of Westbrook, Me. The MVS® Sample Solutions included a common, fixed blue dye (chromophore) concentration and a variable red dye (chromophore) concentration. MVS® Diluent contained the same blue dye concentration as in the MVS® Sample Solutions. The concentrations of red and blue dyes in each of the Sample Solutions and the Diluent are known and well controlled through a rigorous quality control process.

The MVS® Diluent and Sample Solutions are characterized by the absorbance per pathlength values for their red and blue dyes, as defined in Equations (11) and (12). Considering the known absorbance per pathlength of red dye ($a_s$) in each MVS® Sample Solution, the table of FIG. 1 reports the approximate dilution range that may be achieved for each Solution. These dilution ranges are based upon maintaining a measurable absorbance of a mixture of a Sample Solution and Diluent of between 0.3 and 2.4. The $a_s$ in each MVS® Sample Solution was determined through a large volume gravimetric dilution process. A large volume dilution was gravimetrically made for each MVS® Sample Solution using a 5-place analytical balance (Mettler-Toledo, AX205), and the absorbance of this dilution was measured with a horizontal beam UV-Vis spectrophotometer (Varian, Cary 5000) in a cuvette of known pathlength. By making an accurate gravimetric dilution having an absorbance which was within the measurable range of the spectrophotometer, an equivalent $a_s$ value was determined for highly concentrated MVS® Sample Solutions.

200 µL of undiluted (neat) MVS® Sample Solution was dispensed from the multichannel pipette under test into each well in column 1 of an SBS standard 96-well microtiter plate (Costar, 3631). 100 µL of the Sample Solution was aspirated from each well of column 1 using the multichannel pipette and each one of these aliquots of Sample Solutions was dispensed into a separate well of column 2, which contained 100 µL of MVS® Diluent solution. Each of the contents of the wells in column 2 were mixed by aspirating and dispensing 100 µL three times. A 67 µL volume was aspirated from each well of column 2 and each one of these mixtures of Diluent and Sample Solutions was dispensed into column 3, which contained 133 µL of MVS® Diluent, and the mixing step was repeated for the contents of all wells of column 3. This process continued for columns 3 thru 7, with the exception that a different volume of the mixture of Diluent and Sample Solution was dispensed into the wells of each column, as defined in the table of FIG. 2. The absorbance of each solution-filled well was measured at 520 nm and 730 nm using a microtiter plate reader (Bio-Tek Instruments, ELx800nb).

This protocol was followed for all five MVS® Sample Solutions, meaning five separate microtiter plates were prepared, one for each MVS® Sample Solution. All five MVS® Sample Solutions were used to ensure a measurable absorbance for each step of the defined protocol, thus allowing for testing the individual steps of the multi-step dilution protocol defined in the table of FIG. 2.

The table of FIG. 3 summarizes the performance of the multichannel pipette when conducting the defined dilution protocol, and consists of data compiled from all five plates used in this experimental protocol. The inaccuracies of the average dilution ratio are reported, which are based upon the average dilution of the n=8 wells in each column. The measured dilution inaccuracy was calculated versus the target dilution using the formula: Inaccuracy=(Measured−Target)/Target. While only the average inaccuracies are reported herein, the inaccuracy on a tip-to-tip basis may also be determined, which would allow for the analysis of channel-to-channel repeatability for the multi-channel pipette.

The 'Inaccuracy of Stepwise Dilution' data of FIG. 3 shows the uncertainty of the transfer of sample from one column to the next. This inaccuracy calculation was based upon the dilution ratio calculated using Equation (34). The 'Inaccuracy of Total Dilution' of FIG. 3 represents the error associated with the overall dilution ratio for a specific column with respect to column 1, and was calculated using the dilution ratio from Equation (38).

Example One shows that by using the third primary method embodiment of the present invention, it is possible to determine the accuracy of each step of a variable step dilution protocol. Additionally, when using the MVS® Sample Solutions, the data collected indicate that the assumed 1:2000 endpoint dilution ratio can be achieved. In fact, if the acceptable absorbance range for the Range E solution is lowered to 0.19, the measurable dilution ratio extends to almost 1:3000. While an absorbance of 0.19 is measurable for most spectrophotometers, the effect of noise in that measurement should not be ignored.

While a fluorescence-based method could allow for dilution testing beyond a 1:10,000 ratio, the range covered by the MVS® Sample Solutions should allow for testing many commonly performed dilution assays. If a dye with a higher molar absorptivity is used, the testable dilution range could be expanded significantly. For example, many heme porphyrins have a molar absorptivity ($\epsilon$) of >100,000 $M^{-1}cm^{-1}$, which is five times greater than the $\epsilon$ for the red dye used in the MVS® Sample Solution. Using such a dye would clearly increase the testable dilution range to nearly 1:10,000 for this absorbance-based approach.

It should be noted that the results of this approach are independent of several factors, including: i) well size, ii) well shape, iii) well material, and iv) the interaction effects between the solution and the plate material, such as meniscus and air pockets, unless the light beam is obstructed. It should also be noted that this process is highly dependent upon the thoroughness of mixing, as are all dilution based methods. The best performance of any assay based upon dilution schema or upon photometric or fluorometric measurements requires complete mixing, which should be independently assessed.

Example TWO

The process of Example Two included the use of the plurality of MVS® Diluent and Sample Solutions described in Example One and is summarized in representative form in the table of FIG. 4. Generally, 200 μL of undiluted (neat) MVS® Sample Solution was dispensed into each well of column 1 of a 96-well plate (i.e., into 8 wells total). 100 μL of the Sample Solution was aspirated from each well of column 1 using the multichannel pipette of Example One and dispensed into the corresponding wells of column 2, each of which contained 100 μL of Diluent solution. The contents of the wells in column two were then mixed by aspirating and dispensing 100 μL three times. 100 μL of the contents of each well of column 2 were aspirated and dispensed into the corresponding wells of column 3, each of which contained 100 μL of Diluent solution. The mixing step was then repeated for column 3. These steps were repeated across the plate resulting in 1:2 dilution steps for each well. The 100 μL sample aspirated from column 12 (i.e., the last column of the plate filled) was discarded to waste. The plate was then mixed on an orbital shaker at 1300 RPM for one minute. The same protocol was followed using new plates for all five MVS® Sample Solutions. Since these five MVS® Sample Solutions increase in concentration (i.e., from "Range A" through "Range E") to allow low volume measurement with a maintained absorbance response, all dilution steps could be tested and measured.

Based on the known concentrations of MVS® Sample Solutions, the following dilution ranges were possible while maintaining an absorbance response between 0.3 and 2.4 absorbance units: 1) Range A=1 to 1/4 dilution, 2) Range B=1/4 to 1/20 dilution, 3) Range C=1/20 to 1/100 dilution, 4) Range D=1/100 to 1/400 dilution, and 5) Range E=1/400 to 1/2000 dilution.

All five Sample Solutions were analyzed starting from their neat form by performing 1:2 dilutions across an entire 96-well microtiter plate. Individual plates were filled for each solution. The appropriate Sample Solution was used for each dilution to ensure the proper absorbance response based on the calculated dilution range of the solution, as described above. Averages are reported herein. However, inaccuracy on a tip-to-tip basis may be determined, which allows for the analysis of channel-to-channel repeatability reported as '% CV tip-to-tip' in the table of FIG. 4. 'Inaccuracy from initial' represents the error associated with the overall dilution ratio relating the initial dispense in column 1 and a specific column as calculated by Equation (38). 'Inaccuracy of transfer' data shows the uncertainty of the transfer of sample from one column to the next as calculated by Equation (34). Example Two shows that it is possible to determine the accuracy of each step of a serial dilution protocol up to a 1:2000 endpoint ratio by using the third primary method embodiment of the present invention.

Example THREE

Example Three demonstrates the use of the two stepwise dilution calculations presented in Equations (36) and (41) and is represented by the table of FIG. 5. The method of Example Three was not carried out in the same fashion as in the previous two Examples, wherein dilutions were produced from one well to the next in a microtiter plate. Instead, to minimize errors associated with making dilutions, gravimetric dilutions were made of MVS Range C Sample Solution ("Range C"). Three dilutions were gravimetrically made. The first dilution was a 1:20 fold dilution of Range C, made by weighing a desired amount of Range C into a bottle, followed by weighing the desired amount of MVS Diluent. The components were mixed. After mixing, a 1:2 dilution of the mixed sample was performed gravimetrically into a new bottle, and the contents were mixed. A third 1:2 dilution was performed into yet a new bottle. This resulted in three dilutions of Range C; 1:20, 1:40, 1:80.

Each of the three dilutions of Range C were dispensed into all wells of three 96-well microtiter plates using a multichannel pipette such that each dilution of Range C was included in a separate plate. The total volume of each dilution dispensed into each well was 200 μL. After filling all wells, each of the three plates was mixed using an orbital mixer; the purpose for mixing was to evenly spread the solution meniscus. After mixing, the absorbance of all wells in each plate was measured at 520 nm and 730 nm.

The dilution step for each plate was calculated using Equations (36) and (41), as presented in the table of FIG. 5. Unlike the previous Examples, the stepwise dilutions calculated with Equation (36) did not involve comparing the measured absorbance from one column of wells in one plate to another column of wells in the same plate. Instead, the average absorbance of all 96 wells in each plate was calculated, and the stepwise dilutions were calculated from one plate to the next.

Some important items to note from this example are: 1) The first 1:20 dilution step of Range C is not measurable using Equation (36) because the absorbance of the Range C Sample Solution is too high to be directly measured, as demonstrated in FIG. 1. However, this 1:20 dilution step is measurable by Equation (41), as expected. 2) A direct comparison of the stepwise dilution approaches presented in Equations (36) and (41) can be made, and should be equivalent for the experiment performed herein. The data indicates that these two calculations are equivalent, demonstrating the validity of both approaches.

The present invention is also embodied in a kit in one or more forms. The kit of the present invention may include any one or more components of the system of the invention. For example, the kit may include the sample solution, the diluent, the first chromophore, the second chromophore, the diluent chromophore, the sample solution chromophore, the microtiter plate, and/or the vessel. When the kit includes the diluent, the first chromophore, the second chromophore, the diluent chromophore, the sample and/or the solution chromophore, and also includes the microtiter plate and/or the vessel, the included diluent, the first chromophore, the second chromophore, the diluent chromophore, and/or the sample solution chromophore may be contained in the micotiter plate and/or the vessel.

Further, the kit may include instructions for carrying out one or more of the methods described herein using one or more of the systems described herein or other systems suitable to carry out the steps of the methods described. The kit of the present invention also may further include computer-executable software stored on a computer-readable medium, the computer-executable software being capable of performing any one or more of the calculations steps described herein and/or to effect automated performance of one or more steps described.

For example, the computer-executable software may include computer-readable signals tangibly embodied on the computer-readable medium, where such signals define instructions for processing data obtained by carrying out the method of the invention. Such instructions may be written in any of a plurality of programming languages, for example, Java, XML, Visual Basic, C, or C++, Fortran, Pascal, Eiffel, BASIC, COBOL, and the like, or any of a variety of combinations thereof. The computer-readable medium on which such instructions preferably reside is to be compatible with the central processing unit of the computing system. Further, the steps of processing the data may be performed in alternative orders, in parallel and serially.

It is to be understood that various modifications may be made to the method, system and/or the kit without departing from the spirit and scope of the invention. For example, the steps of the method may be performed in differing order, one or more steps may be omitted, and one or more steps may be replaced with alternative forms thereof. Accordingly, other embodiments are within the scope of the claims appended hereto.

What is claimed is:

1. A method of determining the dilution achieved in carrying out a dilution protocol using a sample solution and a diluent, wherein the sample solution includes a first chromophore that absorbs light at a first wavelength and a known concentration of a second chromophore that absorbs light at a second wavelength, the method comprising the steps of:
   a. adding to a first vessel of a first set of a plurality of vessels a target volume of a first sample solution, wherein the first sample solution includes a first known concentration of the first chromophore and a known concentration of the second chromophore, wherein each of the first chromophore and the second chromophore has an absorbance maximum, the absorbance maximum of the first chromophore minimally overlapping with the absorbance maximum of the second chromophore;
   b. adding to a first vessel of a second set of the plurality of vessels a target volume of a second sample solution including a second known concentration of the first chromophore and the known concentration of the second chromophore, wherein the second known concentration of the first chromophore of the second sample solution is higher than the first known concentration of the first chromophore of the first sample solution, and wherein the target volume of the second sample solution added to the first vessel of the second set is substantially equivalent to the target volume of the first sample solution added to the first vessel of the first set;
   c. carrying out a first dilution protocol step comprising:
      i. mixing into the first vessel of the first set a first target volume of a diluent, wherein the diluent includes the second chromophore at a concentration substantially equivalent to the known concentration of the second chromophore in the first sample solution and the second sample solution;
      ii. mixing into the first vessel of the second set the first target volume of the diluent; and
      iii. measuring the absorbance of the first chromophore at the first wavelength and the absorbance of the second chromophore at the second wavelength in the first vessel of the first set;
   d. carrying out a second dilution protocol step comprising:
      i. transferring a target volume of the mixture of the first sample solution and the diluent of the first vessel of the first set to a second vessel of the first set;
      ii. mixing a second target volume of the diluent into the second vessel of the first set;
      iii. transferring a target volume of the mixture of the second sample solution and the diluent of the first vessel of the second set to a second vessel of the second set;
      iv. mixing the second target volume of the diluent into the second vessel of the second set; and
      v. measuring the absorbance of the first chromophore at the first wavelength and the absorbance of the second chromophore at the second wavelength in the second vessel of the second set; and
   e. calculating a dilution ratio of the dilution protocol based on the absorbance measurements made in steps c.iii and d.v, wherein the dilution ratio represents the extent of dilution occurring between the first dilution protocol step and the second dilution protocol step.

2. The method of claim 1 wherein the calculation of the dilution ratio involves using the equation:

$$R'_{12} = \frac{\left(\frac{a_{s_2}}{a_{d_2}}\right) \cdot \left(\frac{A_{2,\lambda_2}}{A_{2,\lambda_1}}\right)}{\left(\frac{a_{s_1}}{a_{d_1}}\right) \cdot \left(\frac{A_{1,\lambda_2}}{A_{1,\lambda_1}}\right)}$$

where $(R'_{12})$ represents the dilution ratio achieved after completing the second dilution protocol step, $(a_{s_1})$ is the absorbance per pathlength of the first chromophore at the first wavelength in the first sample solution, $(a_{s_2})$ is the absorbance per pathlength of the first chromophore at the first wavelength in the second sample solution, $(a_{d_1})$ is the absorbance per pathlength of the second chromophore at the second wavelength in the diluent of the first set; $(a_{d_2})$ is the absorbance per pathlength of the second chromophore at the second wavelength in the diluent of the second set, $(A_{1,\lambda 1})$ is the absorbance of the first chromophore at the first wavelength measured in the first vessel of the first set, $(A_{1,\lambda 2})$ is the absorbance of the second chromophore at the second wavelength measured in the first vessel of the first set, $(A_{2,\lambda 1})$ is the absorbance of the first chromophore at the first wavelength measured in the second vessel of the second set, and $(A_{2,\lambda 2})$ is the absorbance of the second chromophore at the second wavelength measured in the second vessel of the second set.

3. The method of claim 1 further comprising the steps of:
   a. repeating X more times the dilution protocol steps of i) transferring the sample solution and the diluent mixture to subsequent vessels for each of the first and second sets; ii) mixing a target volume of the diluent into the subsequent vessels and iii) measuring the absorbances of the first and second chromophores, wherein X is $\geq 1$, such that the last dilution protocol step is dilution protocol step n and a preceding dilution protocol step is dilution protocol step m, and wherein vessels of the first set and the second set containing the mixture of the sample solution and the diluent after completing dilution protocol step m are represented as vessel m and vessels of the first and second set containing the mixture of the sample solution and the diluent after completing dilution protocol step n are represented as vessel n; and
   b. calculating a dilution ratio of the dilution protocol based on the absorbance measurements made after completing dilution protocol step m and dilution protocol step n, wherein the dilution ratio represents the extent of dilution occurring between dilution protocol step m and dilution protocol step n.

4. The method of claim 3 wherein the calculation of the dilution ratio involves using the equation:

$$R_{m_i n_j} = \frac{\left(\frac{a_{s_j}}{a_{d_j}}\right) \cdot \left(\frac{A_{n_j,\lambda_2}}{A_{n_j,\lambda_1}}\right)}{\left(\frac{a_{s_i}}{a_{d_i}}\right) \cdot \left(\frac{A_{m_i,\lambda_2}}{A_{m_i,\lambda_1}}\right)}$$

where ($Rm_i n_j$) represents the dilution ratio achieved after completing dilution protocol step n, ($as_i$) is the absorbance per pathlength of the first chromophore at the first wavelength in the first sample solution, ($as_j$) is the absorbance per pathlength of the first chromophore at the first wavelength in the second sample solution, ($ad_i$) is the absorbance per pathlength of the second chromophore at the second wavelength in the diluent of the first set; ($ad_j$) is the absorbance per pathlength of the second chromophore at the second wavelength in the diluent of the second set, ($A_{mi,\lambda 1}$) is the absorbance of the first chromophore at the first wavelength measured in vessel m of the first set, ($A_{mi,\lambda 2}$) is the absorbance of the second chromophore at the second wavelength measured in vessel m of the first set, ($A_{nj,\lambda 1}$) is the absorbance of the first chromophore at the first wavelength measured in vessel n of the second set, and ($A_{nj,\lambda 2}$) is the absorbance of the second chromophore at the second wavelength measured in vessel n of the second set.

5. The method of claim 1 wherein the first target volume of the diluent and the second target volume of the diluent are not equal.

* * * * *